(12) United States Patent
Cheng et al.

(10) Patent No.: US 8,551,072 B2
(45) Date of Patent: Oct. 8, 2013

(54) METHODS, DEVICES AND COMPOSITIONS FOR CONTROLLED DRUG DELIVERY TO INJURED MYOCARDIUM

(75) Inventors: Ruth Cheng, Natick, MA (US); Toby Freyman, Waltham, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 935 days.

(21) Appl. No.: 11/954,408

(22) Filed: Dec. 12, 2007

(65) Prior Publication Data

US 2009/0157042 A1 Jun. 18, 2009

(51) Int. Cl.
*A61M 31/00* (2006.01)

(52) U.S. Cl.
USPC ............................................. 604/508

(58) Field of Classification Search
USPC ............... 604/93.01, 103.01, 103.02, 272, 604/500, 507–510, 890.1, 264
See application file for complete search history.

(56) References Cited

U.S. PATENT DOCUMENTS

| | | | |
|---|---|---|---|
| 5,740,808 A * | 4/1998 | Panescu et al. | 600/424 |
| 5,961,459 A * | 10/1999 | Kaul et al. | 600/439 |
| 6,042,820 A | 3/2000 | Sokoll et al. | |
| 6,129,705 A * | 10/2000 | Grantz | 604/103.02 |
| 6,416,739 B1 | 7/2002 | Rogerson et al. | |
| 6,451,349 B1 | 9/2002 | Robinson et al. | |
| 6,545,097 B2 | 4/2003 | Pinchuk et al. | |
| 6,720,008 B2 | 4/2004 | Allison | |
| 6,855,770 B2 | 2/2005 | Pinchuk et al. | |
| 6,899,731 B2 | 5/2005 | Li et al. | |
| 7,014,654 B2 | 3/2006 | Welsh et al. | |
| 7,105,175 B2 | 9/2006 | Schwarz | |
| 7,195,780 B2 | 3/2007 | Dennis et al. | |
| 7,247,319 B2 | 7/2007 | Ramstack et al. | |
| 2004/0001890 A1 | 1/2004 | Rosenblatt et al. | |
| 2004/0213756 A1 * | 10/2004 | Michal et al. | 424/78.17 |
| 2004/0215169 A1 | 10/2004 | Li | |
| 2005/0129727 A1 | 6/2005 | Weber et al. | |
| 2005/0175709 A1 | 8/2005 | Baty, III et al. | |
| 2005/0220853 A1 | 10/2005 | Dao et al. | |
| 2006/0034923 A1 | 2/2006 | Li et al. | |
| 2006/0078624 A1 | 4/2006 | Zalipsky et al. | |
| 2006/0177416 A1 | 8/2006 | Turnell et al. | |
| 2006/0246524 A1 | 11/2006 | Bauer et al. | |
| 2006/0280858 A1 | 12/2006 | Kokish | |
| 2008/0300573 A1 * | 12/2008 | Consigny et al. | 604/509 |

FOREIGN PATENT DOCUMENTS

WO 0224248 3/2002

OTHER PUBLICATIONS

Bala et al., "PLGA Nanoparticle in Drug Delivery: The State of the Art," Department of Pharmaceutics, National Institute of Pharmaceutical Education and Research, p. 387-422 (2004).
Gradus-Pizlo Irmina et al., "Local delivery of biodegradable microparticles containing colchicine or a colchicine analogue: Effects on restenosis and implications for catheter-based drug delivery," Journal of The American College of Cardiology, 26 (1995) 1549-1557.
Wilensky R. L. et al., "Methods and devices for local drug delivery in coronary and peripheral arteries," Trends in Cardiovascular Medicine, Elsevier Science, New York NY, 3 (1993) 163-170.

* cited by examiner

*Primary Examiner* — Kami A Bosworth
(74) *Attorney, Agent, or Firm* — Vidas, Arrett & Steinkraus, P.A.

(57) ABSTRACT

A method for modulating remodeling of an infarct region of a myocardium, the method including the controlled local delivery of therapeutic agent(s) employing microparticles as a carrier, and devices and compositions relating thereto.

13 Claims, 13 Drawing Sheets

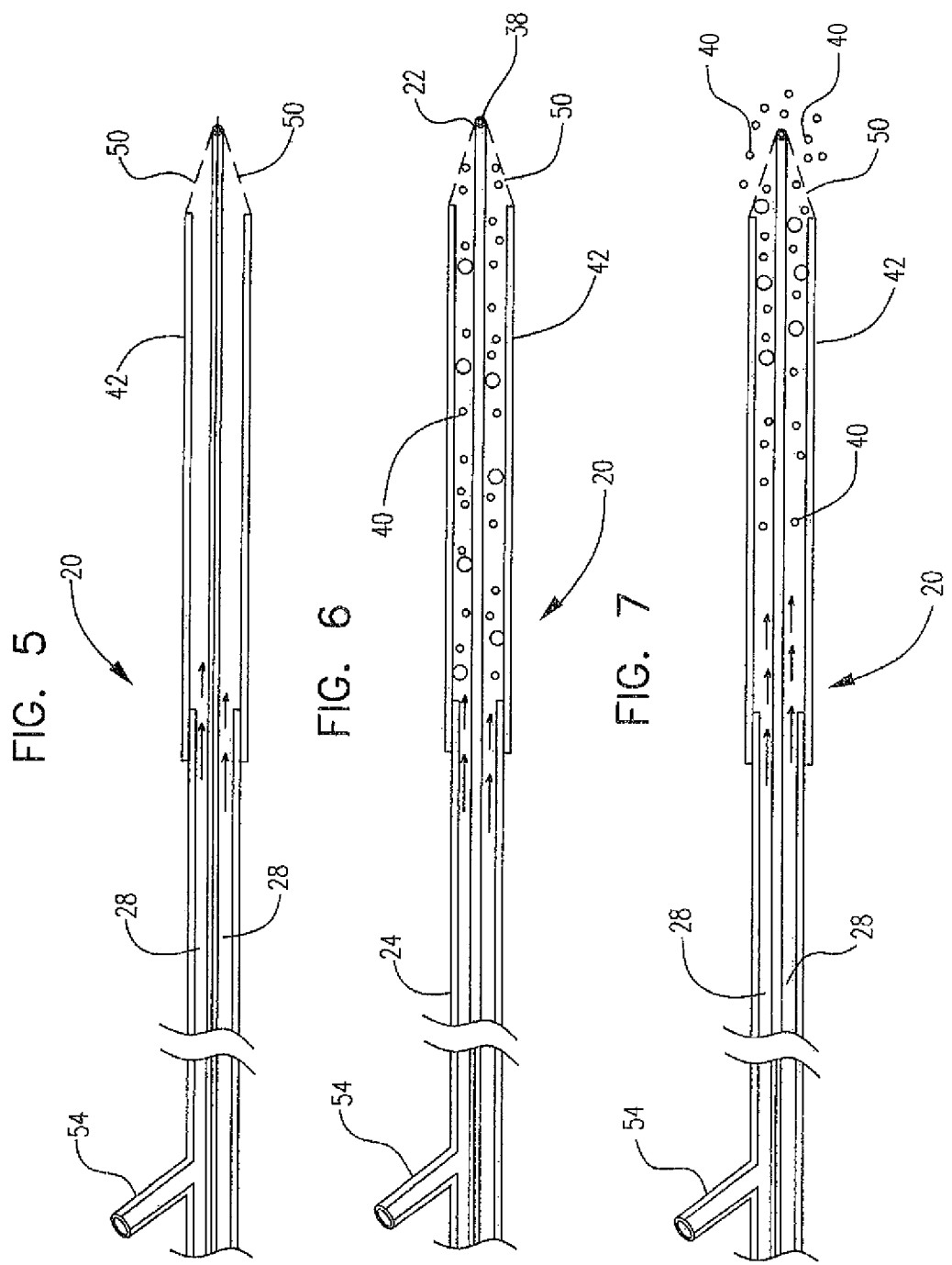

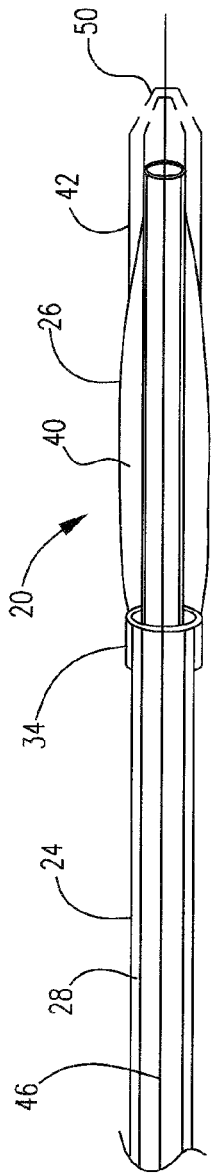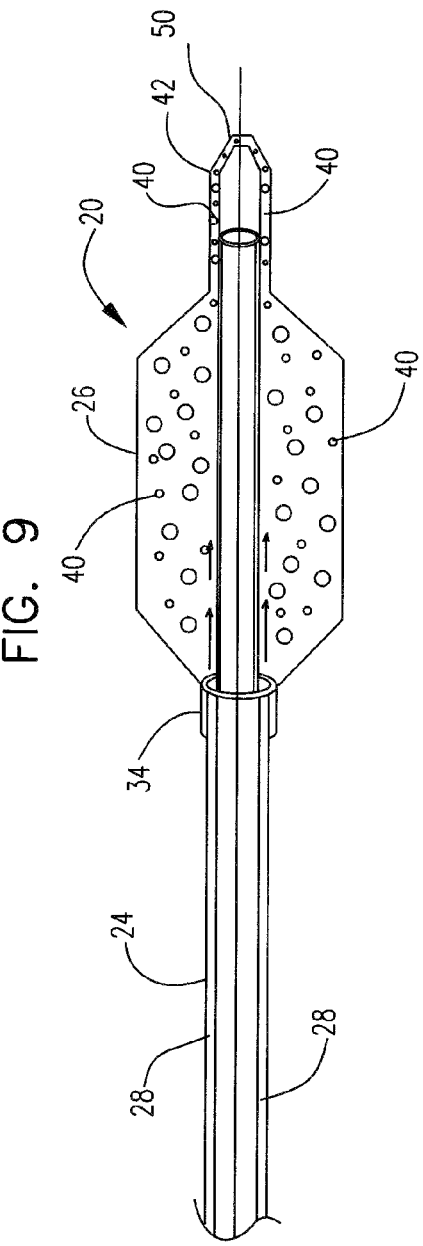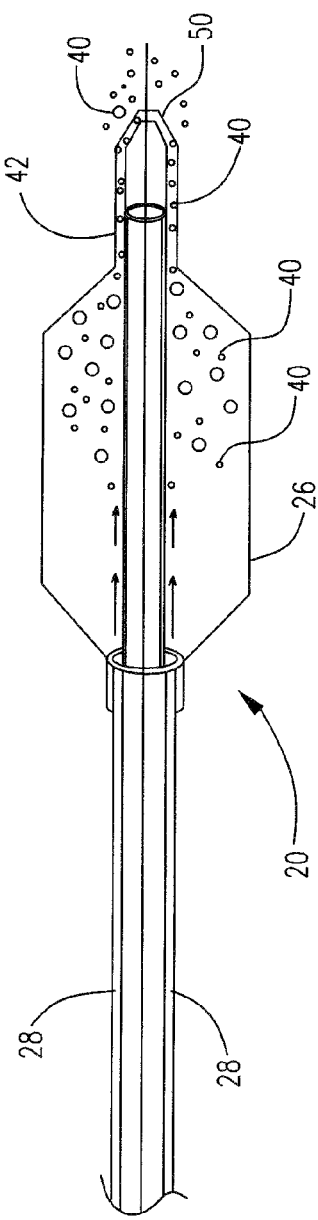

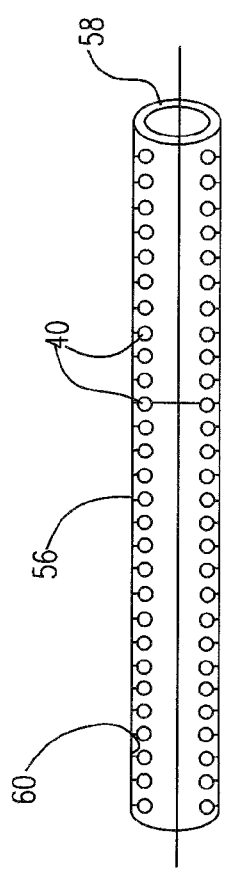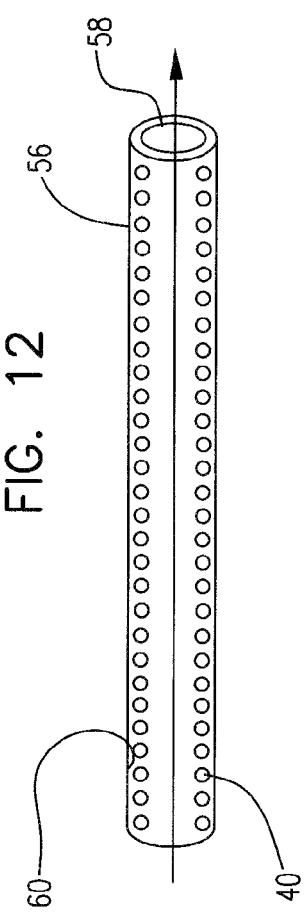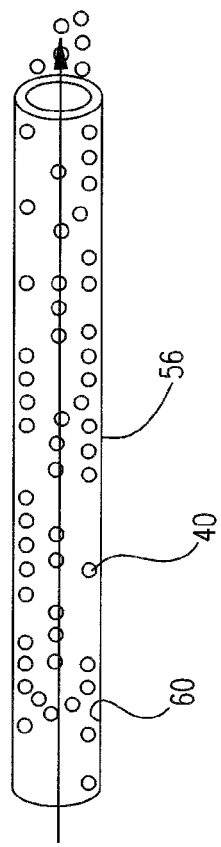

METHODS, DEVICES AND COMPOSITIONS FOR CONTROLLED DRUG DELIVERY TO INJURED MYOCARDIUM

FIELD OF THE INVENTION

The present invention relates to the treatment of infarcted myocardium using controlled local drug delivery, and to methods, devices and compositions for such delivery.

BACKGROUND OF THE INVENTION

Ischemic heart disease is typically the result of an insufficient supply of blood to the heart muscle or myocardium often caused by constriction or obstruction of the blood vessels. For example, progressive artherosclerosis with increasing occlusion of coronary arteries leads to a reduction in coronary blood flow. Hypoperfusion, vasospasm and thrombosis can lead to a further decrease in blood flow.

Myocardial infarction (MI) occurs when the blood supply to the heart is suddenly interrupted which results in insufficient oxygen and other nutrients.

Systemic delivery of drugs for the treatment of myocardial infarction has been relatively effective. However, a significant portion of the population ultimately develops heart failure post-MI. Remodeling of the heart muscle such as the right or left ventricle, post-MI, is a significant component of the progression to heart failure due to uneven stress and strain distribution of the left ventricle post-MI.

Principle components of the remodeling event include myocyte death, edema and inflammation, followed by fibroblast infiltration and collagen deposition, and finally scar formation. The principle component of scar tissue is collagen.

Myocyte loss is a major etiologic factor of wall thinning and chamber dilation that may ultimately lead to progression of cardiomyopathy, a heart disease wherein the heart muscle, typically the left ventricle, is abnormally enlarged, thickened and/or stiffened, which can result in impairment of the heart muscle's ability to pump blood.

The controlled local delivery of drugs has become increasingly desirable because higher doses can be maintained locally and the delivery of drugs directly to diseased tissue can be sustained over a longer period of time, can minimize side effects and is more effective against destructive myocardial remodeling post-MI.

SUMMARY OF THE INVENTION

The present invention relates to devices, methods and compositions for the modulation of remodeling of an infarct region of the myocardium post-myocardial (MI) infarction.

In one aspect, the present invention relates to a method for the controlled delivery of therapeutic agents into the myocardium for modulating remodeling of an infarct region of the myocardium post-MI, the method including inserting a catheter into the myocardium, infusing at least one therapeutic agent into the infarct region, the at least one therapeutic agent effective for modulating remodeling of the infarct region.

Suitably, the carrier for the at least one therapeutic agent are polymeric microparticles or nanoparticles hereinafter referred to as particles. The therapeutic agent may be encapsulated or entrapped in the particles, evenly distributed throughout the particles, or coated or adsorbed on the surface of the particles.

Suitably, for delivery in the vasculature the particles are in the microparticle size range having an average particle size of about 10 to about 25 microns in diameter, although for some applications this range may be varied.

Nanoparticles are also suitable for use in some embodiments described herein and generally have a diameter of about 1000 nm or less suitably from about 5 nm to about 750 nm, and more suitably from about 10 nm to about 500 nm.

The particles are suitably formed from a bioresorbable/biodegradable polymeric composition.

Suitably, the at least one microparticles are infused into the lumen of the coronary artery and into the infarct region.

In some embodiments, the controlled delivery of the drug-loaded particle accompanies a vascular interventional procedure.

The present invention also relates to delivery devices for the controlled localized delivery of the drug-loaded particles described herein.

In one embodiment, individual particles are attached to the luminal side of a component of a catheter assembly, for example, the inner luminal surface of a catheter shaft for a perfusion catheter assembly, through a covalent linkage.

In another embodiment, a perfusion catheter assembly is equipped with pores which selectively allow microparticles such as drug-loaded particles of a specific size to pass therethrough, while preventing other larger particles from passing through.

In another embodiment, a perfusion catheter assembly in the form of a pre-loaded sack/balloon is disposed about a catheter shaft and the distal end of the device contains a membrane with pores sized to selectively allow particles such as drug-loaded microparticles of a specific diameter to pass therethrough, while preventing particles of a larger size from passing through.

In another embodiment, drug-loaded particles are perfused out the distal tip of a perfusion catheter assembly, the distal tip having pores for selectively allowing particles of a specific size to pass therethrough.

The methods, devices and compositions according to the invention can be employed in a variety of procedures including percutaneous coronary intervention (PCI) procedures, for treatment of peripheral artery disease (PAD), for treatment of diseases of the GI tract, treatment of renal vasculature, etc.

These and other aspects, embodiments and advantages of the present invention will become immediately apparent to those of ordinary skill in the art upon review of the Detailed Description and Claims to follow.

BRIEF DESCRIPTION OF THE DRAWINGS

FIG. 5 is a longitudinal cross-section of the distal end of one embodiment of a perfusion catheter assembly wherein the distal tip is equipped with a porous membrane.

FIG. 6 is a longitudinal cross-section of the distal end of one embodiment of a perfusion catheter assembly similar to that shown in FIG. 5 having perfusate of drug-loaded particles injected therein.

FIG. 7 is a longitudinal cross-section of the distal end of one embodiment of a perfusion catheter assembly similar to that shown in FIGS. 5 and 6 showing a perfusate of drug-loaded particles perfusing therethrough.

FIG. 8 is a longitudinal cross-section of the distal end of one embodiment of a perfusion catheter assembly with the perfusion balloon in a deflated state.

FIG. 9 is a longitudinal cross-section of the distal end of a perfusion catheter assembly similar to that shown in FIG. 8 with the perfusion balloon in an inflated state.

FIG. 10 is a longitudinal cross-section of the distal end of a perfusion catheter assembly similar to that shown in FIGS. 8 and 9 with the perfusion balloon in an inflated state illustrating drug-loaded particles perfusing through a membrane located on the distal tip.

FIG. 11 is a longitudinal cross section of a tubular member which may be employed for a variety of perfusion catheter assembly components, the tubular member having drug-loaded particles disposed on the inner lumen.

FIG. 12 is a longitudinal cross section of a tubular member similar to that shown in FIG. 11 illustrating perfusion of a solution therethrough.

FIG. 13 is a longitudinal cross section of a tubular member similar to that shown in FIGS. 11 and 12 illustrating perfusion of the drug-loaded particles out of a membrane on the distal end of the tubular member.

DETAILED DESCRIPTION OF THE INVENTION

Figure 1:
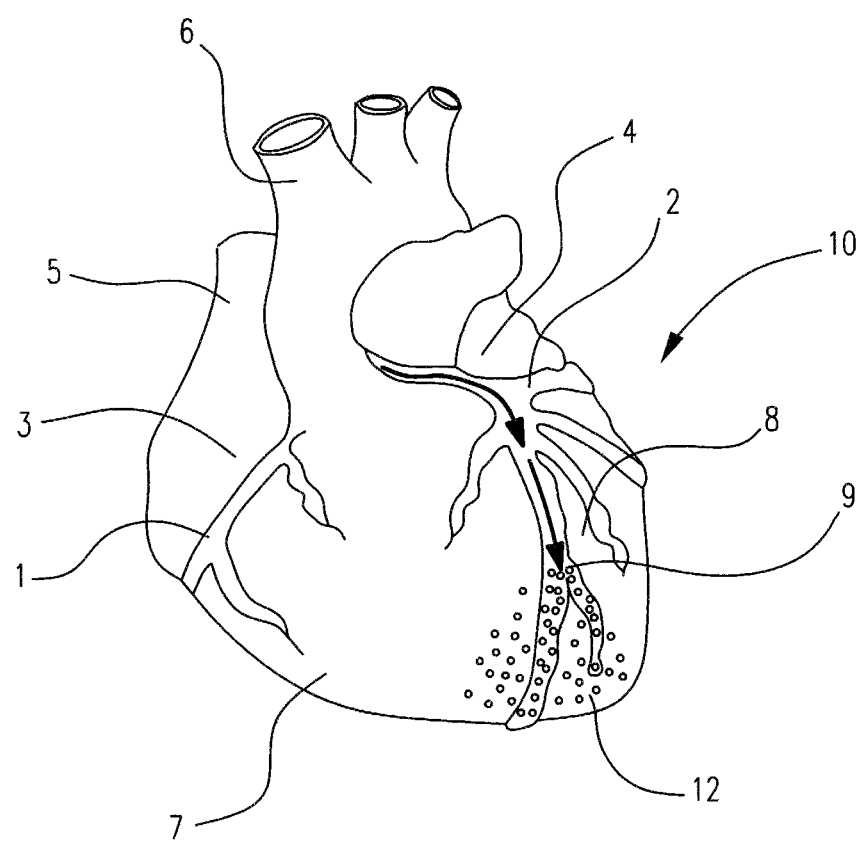
FIG. 1 is a schematic diagram of the heart showing therapeutic agent delivery by intracoronary infusion.

While this invention may be embodied in many different forms, there are described in detail herein specific preferred embodiments of the invention. This description is an exemplification of the principles of the invention and is not intended to limit the invention to the particular embodiments illustrated.

All U.S. patents and applications and all other published documents mentioned anywhere in this application are incorporated herein by reference in their entirety. Any copending patent applications, mentioned anywhere in this application are also hereby expressly incorporated herein by reference in their entirety For the purposes of this disclosure, like reference numerals in the figures shall refer to like features unless otherwise indicated.

In one aspect the present invention relates to the controlled local delivery of therapeutic agent(s) to an injured myocardium for modulation of remodeling of the myocardium post-MI using polymeric particles as a carrier for the therapeutic agent(s). FIG. 1 is a schematic diagram illustrating a myocardium 10 post-MI. Myocardium 10 includes right coronary artery 1, left coronary artery 2, right atrium 3, left atrium 4, superior vena cava 5, aorta 6, right ventricle 7, left ventricle 8, and left anterior descending (LAD) 9. Particles 20 are infused into a lumen of a major coronary vessel, in this embodiment the left anterior descending (LAD), and directly to the infarct region 12. In this embodiment, the infarct region 12 is shown in the left ventricle 8. Local delivery of the therapeutic agent(s) to the infarct region 12 may be beneficial because the drug delivery process has little or no impact on the surrounding healthy heart tissue. The therapeutic benefit is in the prevention of the loss of function of the myocardium in the region of the injury due to remodeling and scar formation which occurs as a result of the natural reparation process of the infarct post-MI which can ultimately result in thinning of the ventricular wall.

FIG. 1 is intended for illustrative purposes only. The present invention can be employed for delivery of therapeutic agents to other areas of the body as well, and in particle to other regions of the heart. For example, the present invention can be employed to deliver therapeutic agent to the heart through the circumflex branch of the coronary artery to the back of the left ventricle and through the right coronary artery to treat either of the ventricles, the right atrium and the sinoatrial node as well.

In this embodiment, the particles 20 are suitably in the microparticle size range, the microparticles 20 suitably having a diameter in the range of about 10 microns to about 25 microns, and more suitably about 10 microns to about 20 microns. The particles may be of a mixed population according to size within the stated range, or may have a uniform size population based on average diameter in the stated range. For example, the microparticles may have a mixed size population within a range of about 10 microns to about 25 microns, or the microparticles may have a uniform population with an average diameter of about 15 microns±1.5 microns. Delivery of microparticles having a size of greater than about 25 microns can have a negative impact on the coronary blood flow. For example, microparticles having an average diameter of about 30 microns or greater may result in ischemia due to microvascular plugging.

In this embodiment, the total mass of microparticles delivered in a single bolus of drug loaded microparticles is suitably about 10 mg or less. The infusion of a greater mass of microparticles can negatively impact the coronary blood flow.

In this embodiment, the number of particles delivered in a single bolus is suitably between about $5\times10^5$ to about $1\times10^7$ for maintaining optimum therapeutic effect without any significant impact on the coronary blood flow. Therapeutic effect may be acute, chronic or both. For example, the drug released from these microparticles may limit post-MI remodeling over a span of weeks. Depending on the therapeutic agent delivered, there can be acute cardioprotective effect.

The total number of particles delivered is also dependent on average particle size. For smaller particles, a larger number of total particles may be delivered. For particles having an average particle size of about 10 microns, up to about $1\times10^7$ particles may be delivered. For particles having an average particle size of about 20 microns, up to about $1\times10^6$ total particles may be delivered. For average particle sizes between about 10 microns and about 20 microns, the desirable number of particles delivered may vary.

The particles may be formed from any suitable polymer composition including both either non-biodegradable or biodegradable polymers. More suitably, the particles are formed from biodegradable polymer material. The polymer may be natural or synthetic, with synthetic polymers being preferred due to the better characterization of degradation and, where appropriate, release profile of an incorporated agent. The polymer is selected based on the period over which degradation or release of an agent is desired, generally in the range of at several weeks to several months, although shorter or longer periods may be desirable.

Suitable polymer materials that may be incorporated into the polymer composition include, but are not limited to, polyhydroxyalkanoates such as poly(hydroxybutyrate) (PHB), poly(hydroxyvalerate) (PHV) and poly(hydroxybutyrate-co-valerate), polylactones such as polycaprolactone (PCL), poly (L-lactic acid) (PLA), poly(glycolic acid) (PGA), poly(D,L-lactic acid), poly(lactide-co-glycolide) (PLGA), poly (lactide-co-caprolactone), polydioxanone, polyorthoesters, polyanhydrides, poly(glycolic acid-co-trimethylene carbonate), polyphosphoesters, polyphosphoester urethanes, poly (amino acids), cyanoacrylates, poly(trimethylene carbonate), polyurethanes, poly(iminocarbonate), copoly(ether-esters) (e.g. PEO/PLA), polyalkylene oxalates, polyphosphazenes and biomolecules such as fibrin, fibrinogen, starch, collagen, hyaluronic acid, other natural polymers such as alginate, polysaccharides such as dextran and cellulose, etc., and mixtures thereof.

The particles can also be formed from bioerodible hydrogels which are prepared from materials and combinations of materials such as polyhyaluronic acids, casein, gelatin, glutin, polyanhydrides, polyacrylic acid, alginate, chitosan, poly (methyl methacrylates), poly(ethyl methacrylates), poly(butylmethacrylate), poly (isobutyl methacrylate), poly (hexylmethacrylate), poly (isodecyl methacrylate), poly (lauryl methacrylate), poly (phenyl methacrylate), poly(methyl acrylate), poly(isopropyl acrylate), poly(isobutyl acrylate), and poly(octadecyl acrylate).

Other suitable polymers include, but are not limited to, polyvinylpyrrolidone, polyethylene oxide (polyethylene glycol), polyvinyl alcohol, etc.

See, for example, U.S. Patent Publication No. 2006/0078624, for suitable polymer compositions for particle formation, the entire content of which is incorporated by reference herein.

Particulate carriers formed from an α-hydroxy acid and α-amino acid monomers are disclosed in U.S. Pat. No. 6,042,820, the entire content of which is incorporated by reference herein.

In some embodiments, the particles are formed from a polymer composition that includes at least one of L-lactic acid, D,L-lactic acid, glycolic acid, caprolactone, or copolymers thereof.

Preferred biodegradable polymers are polyglycolic acid, polylactic acid, copolymers of glycolic acid and L- or D,L-lactic acid, and copolymers of glycolide and L- or D,L-lactide. Those of skill in the art will appreciate that the molecular weight of the polymer, the ratio of one monomer to another, for example the lactide to glycolide ratio, and the compositions of the end groups can be varied to tailor the properties of the particle.

In some embodiments, polylactide-co-glycolide copolymers are employed in forming the particles. The ratio of lactide to glycolide may range from about 50:50 to about 85:15. In one embodiment, a ratio of 75:25 lactide to glycolide may be employed.

U.S. Patent Publications discussing drug-loaded particles include, for example, U.S. 2005/0220853, the entire content of which is incorporated by reference herein.

The particles may be hollow, i.e. having a polymeric outer shell, they may be solid wherein therapeutic agent may be distributed throughout or coated or other wise bonded on the surface thereof, or they may have more than one phase, for example, a liquid core with a polymeric outer shell.

In one specific embodiment, the particle is a solid polymeric particle having therapeutic agent distributed throughout the polymeric material.

To form a particle having a solid core, the polymer used as polymeric core can be mixed with an effective amount of therapeutic agent(s). This may be referred to as "microencapsulation" of the therapeutic agent(s). Methods of microencapsulation include, but are not limited to, rotating disk, spray drying, fluidized bed, single, double or three-phase emulsion techniques, drop-by-drop, spray drying, phase separation, etc.

An example of rotating disk type microencapsulation method is described in U.S. Patent Publication No. 2004/0001890, the entire content of which is incorporated by reference herein.

Spray-drying is described in U.S. Pat. Nos. 6,451,349 and 6,416,739, each of which is incorporated by reference herein in its entirety.

The particle may also have a solid core with a sustained release coating of therapeutic agent(s) on the outside surface. One way to do this is to dissolve the therapeutic agent(s) with a polymer in a solvent containing both therapeutic agent(s) and polymer and then coating the particle core. See U.S. 2004/0001890, the entire content of which is incorporated by reference herein.

In a specific embodiment, the particles are formed with a poly(lactide-co-glycolide) copolymer having a ratio of 50:50 lactide to glycolide and an ace (angiotensin converting enzyme) inhibitor using a single emulsion technique. The solvent employed may be any suitable organic solvent. Exemplary solvents include methylene chloride and ethyl acetate. The particle size may be controlled by the stir rate as well as by filtering after the particles have been formed. See, for example, U.S. Pat. No. 6,720,008 discussing single emulsion techniques, the entire content of which is incorporated by reference herein in its entirety. Single emulsion techniques are well known. See, for example, U.S. Patent Pub. Nos. 20050175709, 2006/0177416 and 2006/0034923, each of which is incorporated by reference herein in its entirety.

Examples of commercially available polymers having a ratio of 50:50 lactide to glycolide based on mole-% such as MEDISORB® 5050DL available from Alkermes, Inc. in Blue Ash, Ohio and RESOMER® RG 502 available from Boehringer Ingelheim in Germany.

Other suitable commercially available products having different ratios of lactide to glycolide as a mole-% are MEDISORBQR 6535 DL, 7525 DL, 8515 DL and Resomer® KG 752 having a ratio of 75:25 lactide to glycolide and Resomer® KG 206.

Any of these copolymers are available in a wide range of molecular weights and ratios of lactic acid to glycolic acid from about 5,000 daltons to about 500,000 daltons.

Alternatively, for water-soluble drugs, a double emulsion may be employed wherein the first emulsion includes the water soluble drugs in the aqueous phase and the polymer is in the organic phase. A double emulsion method of forming drug-loaded microparticles is described in U.S. Pat. No. 7,247,319, the entire content of which is incorporated by reference herein.

The particles described herein may be employed for localized controlled release of the therapeutic agents, the release of which may be sustained over a period of days, weeks, or even months. The release kinetics can be controlled by both the carrier as well as the therapeutic agent(s) itself.

Any therapeutic agent may be employed herein. As used herein, the terms, "therapeutic agent", "drug", "pharmaceutically active agent", "pharmaceutically active material", "beneficial agent", "bioactive agent", and other related terms may be used interchangeably herein and include genetic therapeutic agents, non-genetic therapeutic agents and cells. A drug may be used singly or in combination with other drugs. Drugs include genetic materials, non-genetic materials, and cells.

In some embodiments, the present invention may be employed for the localized, controlled release of therapeutic agents for modulation of post-MI remodeling. For modulation of post-MI remodeling, some therapeutic agent(s) may be more efficacious than others. Examples of agents useful for the mediation of post-MI remodeling include, but are not limited to, selective or non-selective matrix metalloproteinase inhibitors (MMPi) (tissue inhibitor of metalloproteinases or TIMPs including TIMP-1, TIMP-2, TIMP-3 and TIMP-4), mediation of renin angiotensin aldosterone system (RAAS) pathways and myocardial salvage including the prevention of myocyte death and the promotion of myocyte proliferation, mediation of mitochondrial death pathways and apoptosis, etc.

RAAS may be mediated through the introduction of ACE inhibitors (or inhibitors of angiotensin-converting enzyme), angiotensin receptor antagonists or blockers and aldosterone blockers, for example.

ACE inhibitors may be used to reduce the formation of angiotensin II, the production of which can ultimately result in elevated blood pressure. Examples of ACE inhibitors include, but are not limited to, sulfhydryl-containing ACE inhibitors Captopril such as captopril sold under the tradename of CAPOTEN®, dicarboxylate-containing ACE inhibitors such as quinapril sold under the tradename of ACCUPRIL®, enalapril (VASOTEC®/RENITEC®), Quinapril® (ACCUPRIL®), ramipril (ALTACE®/TRITACE®/RAMACE®/RAMIWIN®), perindopril (COVERSYL®/ACEON®), lisinopril (LISODUR®/LOPRIL®/NOVATEC®/PRINIVIL®/ZESTRIL®), benazepril (LOTENSIN®) and phosphate-containing ACE inhibitors such as fosinopril sold under the tradename of MONOPRIL®.

Angiotensin receptor antagonists include, but are not limited to, losartan COZAAR®), valsartan (DIOVAN®), irbesartan (AVAPRO®), candesartan (ATACAND®) and telmisartan (MICARDIS®).

An example of an aldosterone blockers include, but are not limited to, spironolactone and eplerenone.

Other examples of drugs which may be employed for mediation of remodeling include, but are not limited to statins such as atorvastatin (competitive inhibitors of HMG-CoA reductase), nitroglycerine, and TGF-beta inhibitors, cardioprotective agents, anti-apoptotic agents, adenosine, myofibroblast proliferation/migration/maturation inhibitors, β-blockers such as Carvedilol, NEP (neutral endopeptidase) inhibitors such as omapatrilat, vasopeptidase inhibitors, growth factors such as VEGF, PDGF, IGF, bFGF, SDGF, etc., PPAR (peroxisome proliferator-activated receptor) agonists, anti-inflammatory agents, etc.

Some therapies are suitably administered within about 72 hours of the MI event as this is when some early remodeling of the heart muscle may occur, while other therapies may be delivered beyond 72 hours, for example, up to about 2 weeks. As an example only, ACE inhibitors and therapies for mediation of RAAS pathways may suitably be delivered within about 72 hours. Suitably, matrix metalloproteinase inhibitors are delivered within about one week, and more suitably within about 72 hours.

The mediation of early remodeling by the controlled local delivery of select therapeutic agents can be particularly efficacious because infarct expansion may occur early and results in ventricular dilatation and wall thinning, and causes elevation of diastolic and systolic wall stresses (increased blood pressure).

The present invention may be employed at the same time as vessel reperfusion, immediately after vessel reperfusion or as a separate interventional procedure. Suitably, however, local drug delivery is employed concurrently with or immediately after an interventional procedure such as percutaneous coronary intervention (PCI).

Figure 2:
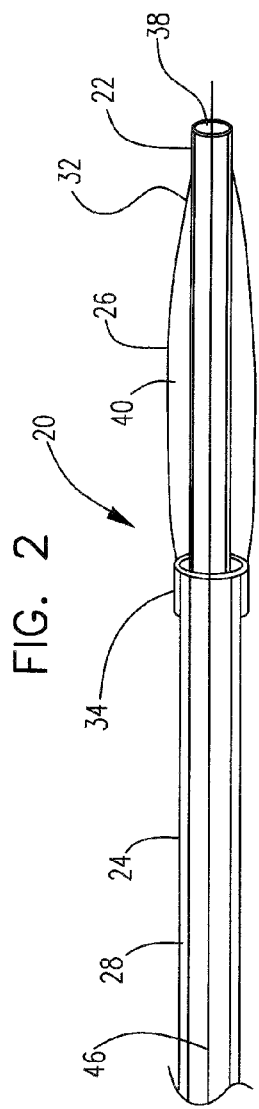
FIG. 2 is a longitudinal cross-section of the distal end of one embodiment of a perfusion catheter assembly, the assembly including a perfusion balloon having drug-loaded particles pre-loaded into the balloon, the balloon, in a deflated state, shown mounted on the catheter assembly.
Figure 3:
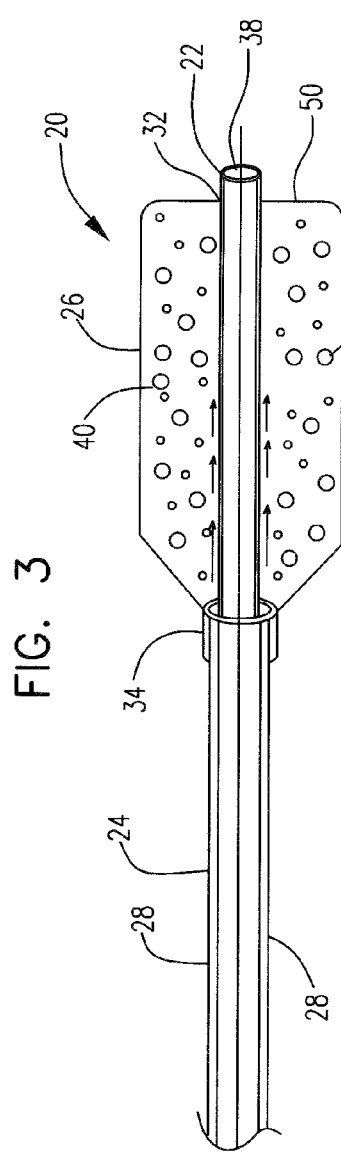
FIG. 3 is a longitudinal cross-section of the distal of an embodiment of a perfusion catheter assembly similar to that shown in FIG. 2 showing a perfusion balloon in an inflated state.
Figure 4:
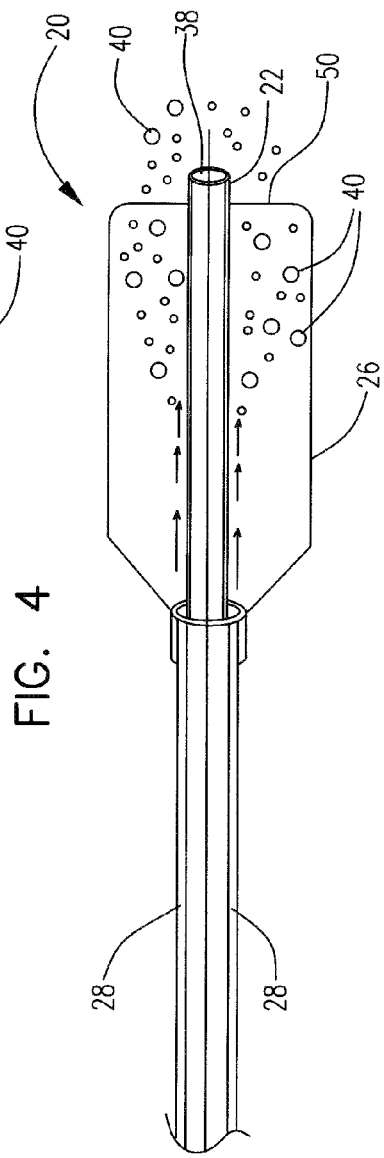
FIG. 4 is a longitudinal cross-section of the distal end of an embodiment of a perfusion catheter assembly similar to that shown in FIGS. 2-3 showing the balloon in an inflated state with drug-loaded particles perfusing therethrough.

Any suitable delivery device may be employed herein. FIGS. 2-4 illustrate one embodiment of a perfusion catheter assembly 20 for delivery of drug-loaded particles 40, suitably in this embodiment in the microparticle size range. Perfusion catheter 20 is a dual-lumen catheter assembly including an inner shaft 22 and an outer shaft 24. Distal end 32 of perfusion balloon 26 is mounted on distal end of inner shaft 22 and the proximal end 34 of perfusion balloon 26 is mounted on distal end of outer shaft 24.

Guide wire 46 is shown within the inner lumen 38 (guide wire lumen 38) defined by inner shaft 22.

Drug-loaded particles 40 are pre-loaded into balloon 26 which is shown in a deflated state in FIG. 2. Balloon 26 may be inflated by perfusing a liquid carrier through lumen 28 of outer shaft 24 and into the balloon indicated by arrows in FIG. 3. The drug-loaded particles become dispersed or suspended in the liquid carrier. Shown at the distal end 32 of balloon 26 is a membrane 50. Membrane 50 has a pore size which allows particles of a certain specified size to pass through, but limits the passage of other larger particles. The pores may be configured to allow particles of only one size, i.e. 15 microns±1.5 microns) or may be configured to allow particles of a certain particle size range, i.e. 10-20 microns, to pass while limiting the passage of larger particles as shown in FIG. 4.

Of course, membrane 50, can be located anywhere on the balloon as desired.

Furthermore, the membrane is provided for illustration only, and the device nor the scope of the invention are limited by this illustrative feature. Any suitable structure can be employed as a substitute for a membrane providing perfusion of selected particle sizes is allowed out of the device, while preventing other particle sizes from entering a patient's system.

Perfusion of the inflation media through the balloon may be pulsatile so as to mix and agitate the particles and to prevent clogging of the membrane.

In use, the drug-loaded particles 40 can be infused into the lumen of the left anterior descending (LAD) 9 and is positioned at the infarcted region 12 as shown in FIG. 1. Using this delivery approach, a guide catheter may be inserted through the femoral artery of a patient, and positioned at the ostium of the left coronary artery 2. The guide catheter is then employed to assist the placement of the balloon catheter assembly into the left coronary artery 10 and into the LAD 9 and into position at the infarct region 12. A guide wire is used to assist this placement.

Balloon 26 may then be inflated as illustrated in FIGS. 2-4 and the drug-loaded particles perfused into the infarct region 12 where they can lodge in the myocardial capillaries and release drug to the surrounding tissue in a controlled, sustained manner. The bioresorbable/biodegradable polymer used for forming the particle 40, whether a hollow shell or a solid particle having drug dispersed throughout the solid, slowly allows the drug to elute over time.

Suitably, the drug-loaded particles are infused into the coronary artery in a single bolus. However, discrete incremental doses can also be employed.

The delivery of the drug-loaded particles can be done concurrently with a vessel reperfusion process such as PCI, immediately after a vessel reperfusion process, or in a separate interventional procedure. Suitably, the particles are delivered at the time of vessel reperfusion for optimum results.

Another embodiment of a perfusion catheter assembly is shown generally at 20 in FIGS. 5-7. Perfusion catheter assembly 20 is a dual lumen catheter assembly having an inner shaft 22 and an outer shaft. Inner shaft 22 defines a guide wire lumen 38. The distal end of the perfusion catheter assembly 20 is equipped with a distal tip 42 which further includes a porous membrane 50. Porous membrane 50 includes pores which are sized so as to allow passage of particles of specific diameter size only. In this embodiment, suitably the size of the particles is in the microparticle size range. Pores can be sized so as to allow particles of only a single diameter size to pass through such as 15 microns±1.5 microns or of a given size range such as about 10 microns to about 20 microns in size while excluding particles of a larger size from passing through.

Again, referring to FIG. 1 for illustration only, the perfusion catheter assembly 20 can be employed to infuse drug-loaded particles 40 into a coronary artery such as the left coronary artery 2, into the lumen of the left anterior descending (LAD) 9 and into the infarcted region 12. Using this delivery approach, a guide catheter may be inserted through the femoral artery of a patient, and positioned at the ostium of the left coronary artery 2. The guide catheter is then employed to assist the placement of the perfusion catheter assembly 20 shown in FIG. 5 into the left coronary artery 10, into the LAD 9 and positioned at the infarct region 12. A guide wire is used to assist this placement.

The proximal end of the catheter assembly 20 may be further equipped with a port 54 for injecting a carrier fluid including the drug-loaded particles dispersed of suspended therein. Drug-loaded particles 40 in the carrier liquid are passed through the distal tip 42 and out through the porous membrane 40.

In one embodiment, the perfusion catheter assembly 20 includes both a balloon 26 and a distal tip 42 as shown in FIGS. 8-10. The distal tip includes porous membrane 40 having pores sized to allow selective perfusion of drug-loaded microparticles or nanoparticles as discussed above. FIG. 8 illustrates the balloon 26 in a deflated, folded, wrapped configuration. Balloon 26 is shown pre-loaded with the particles 40. However, the drug-loaded particles may be injected into the catheter through a port which is in communication with an inflation lumen 28 rather than pre-loading the balloon as well. FIG. 9 illustrates balloon 26 in an inflated state and FIG. 10 illustrates particles of a selected size only being perfused through membrane 50 while larger particles are prevented from perfusing through membrane 50. In this embodiment, the particles are suitably in the microparticle size range.

The catheter may also have more than one or two lumens, as in the case where the catheter includes both an occlusion or angioplasty balloon and a perfusion balloon. Of course, some devices employ two or more balloons as well.

In other embodiments, a perfusion catheter assembly includes drug loaded particles, suitably nanoparticles, that are covalently bonded to the inner lumen of a catheter component. Any suitable component which allows perfusion through the lumen may be employed including both the inner and outer shafts and balloons. Tubular member 56 with inner lumen 58 and inner surface 60 is shown in FIGS. 11-13 having particles 40, suitably nanoparticles, covalently bonded to inner surface 60.

Nanoparticles typically have a diameter of about 1000 nm or less, preferably from about 5 nm to about 750 nm, and more preferably from about 10 nm to about 500 nm.

Suitably, the covalent linkages may be readily cleaved, allowing the drug particles to release. In some embodiments, the linkage is formed so as to be readily cleaved through the use of enzymes. In other embodiments, the linkage is formed so as to be readily cleaved in the presence of water. Cleavage of the covalent linkages allows the drug-loaded nanoparticles to be perfused out of the lumen of the catheter component, to the treatment site within a patient.

A variety of covalent and non-covalent linking methods may be employed for attaching the nanoparticles to the inner lumen surface 60 such as ester and thioester linkages, peptide linkages, and water soluble materials. Such attachment methods are known to those of skill in the art, some of which are listed below. These methods are illustrative only, and are not intended to limit the scope of the present invention in any way.

Ester and thioester linkages can be employed. Such linkages are hydrolyzable, the rate of which can be increased using esterases.

Peptide linkages are readily cleaved by appropriate enzymes.

Other types of covalent bonds, for example amide bonds and siloxane based linkages can also be used to attach the nanoparticle to the device surface.

Disulfide linkages are also readily severable and involve functionalization of the surface of the nano-particles such as with an —SH containing silane and the surface of the device with an activated disulfide linkage.

Alternatively, molecules may be covalently attached via linker molecules. Molecules may also be attached to the surface by non-covalent linkage, for example by absorption via hydrophobic binding or Van der Waals forces, hydrogen bonding, acid/base interactions and electrostatic forces.

Layer-by-layer (LbL) adsorption is one specific method that can be employed in attachment of the drug-loaded nanoparticles wherein the particle is formed using this method and the surface of the device is treated accordingly. Using LbL self-assembly techniques, the sequential absorption of oppositely charged species from solution, e.g. aqueous media, can be employed to prepare multi-layer films. The charge on the outer layer is reversed upon deposition of each subsequent polyelectrolyte layer. These techniques are also known in the art. See for example, commonly assigned US Patent Publication No. 2005/0129727, the entire content of which is incorporated by reference herein.

Other examples of linking methods are provided in U.S. Pat. No. 7,195,780, wherein nanocaps are attached to nanotubes either through the use of covalent linkages or non-covalent techniques, the entire content of which is incorporated by reference herein.

One specific method of binding nanoparticles to the luminal surface of a device is to employ a polyalkylene glycol linker such as the heterobifunctional polyethylene glycol (PEG) liners disclosed in U.S. Patent Pub. No. 2006/0246524, the entire content of which is incorporated by reference herein. Suitably, the nanoparticles are coupled to the PEG via a hydrolyzable linker. This is a well known technique commonly referred to in the art as "PEGylation". Using this technique, chemically active or activated derivatives of the PEG polymer are first prepared to attach the PEG to the desired molecule. The selection of the functional group for the PEG derivative is based on the available reactive group on the molecule that will be coupled to the PEG. Commonly used end groups for heterobifunctional PEGs include, but are not limited to, maleimide, vinyl sulfones, pyridyl disulfide, amine, carboxylic acids and NHS esters. If, for example, PLGA nanoparticles are attached via a PEG linker, no activation may be required. The carboxylic acid groups of PLGA may be directly reacted with PEG. If however, one wishes to attach PLGA via available hydroxyl groups, then PEG may be activated with a sulfonate group, for example. PLGA is shown below:

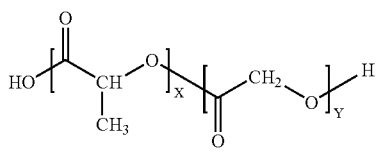

where X is the number of units of lactic acid and Y is the number of units of glycolic acid. For attaching nanoparticles to the luminal surface of a medical device, one would first coat the surface of the device with PEG macromolecules, prior to reacting with the PLGA nanoparticles.

Biocompatible adhesives may also be employed, for example, cyanoacrylates may be employed. Other adhesives include, but are not limited to, polyurethanes, epoxies, polyamides, polyimides, silicones, and so forth. The adhesive may be coated on the inner lumen surface, for example.

Water soluble gels or other hydrogels and fibrin gels may be employed for adhering the nanoparticles on the inner lumen surface.

Figure 14:
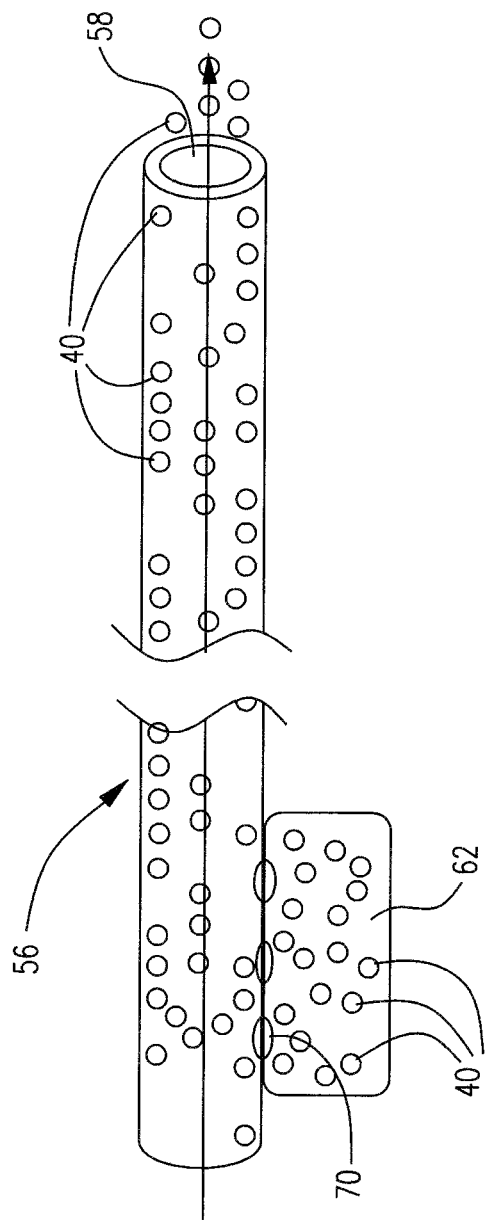
FIG. 14 is a longitudinal a tubular member which may be employed for a variety of perfusion catheter assembly components and a reservoir in fluid communication therewith, the reservoir containing drug-loaded particles.

In another embodiment, illustrated generally in FIG. 14, a delivery catheter assembly may include a reservoir 62 located at the proximal end of component of a catheter assembly. The reservoir 62 is in fluid communication with an inner lumen 58 of a tubular member 56 which may be employed in a catheter assembly for, as an example, an inner shaft (guide wire lumen) or an outer shaft, and extends substantially the entire length of the catheter assembly. Fluid communication can be provided by multiple openings 70 between the reservoir 62 and the lumen 58 of the tubular member 56 which forms part of the catheter assembly. Reservoir 62 contains the carrier liquid with the drug-loaded particles 40 dispersed or suspended therein. As fluid is infused into the lumen, the liquid carrier with drug-loaded particles 40 is pulled from the reservoir into the fluid flow and out the distal end of the lumen 58 as shown in FIG. 14.

Any therapeutic agent may be used in combination with the methods and devices disclosed herein. Examples of drugs which may be delivered using any of the above devices or methods may be found in commonly assigned U.S. Pat. Nos. 7,105,175, 7,014,654, 6,899,731, 6,855,770 and 6,545,097, each of which is incorporated by reference herein in its entirety, and in commonly assigned U.S. Patent Application Publication No. 2004/0215169, the entire content of which is incorporated by reference herein.

The methods, devices and compositions disclosed herein may be employed for any application where it is desirable to have controlled local delivery of drugs. Examples include, but are not limited to, treatment of the coronary vasculature, treatment of the gastrointestinal tract such as for the treatment of Crohn's disease, treatment of the peripheral vasculature, treatment of the renal vasculature such as for renal insufficiency, etc.

The methods, devices and compositions of delivering therapeutic agents locally and for sustained periods of time can eliminate the need for additional procedures and associated complications.

The following non-limiting examples further illustrate some aspects of the present invention.

EXAMPLES

Particles were tested for optimum size, mass and total number of particles to be delivered in a single bolus. In these examples, the particles were polystyrene microparticles having an average particle size between about 10 and about 25 microns. The particles were infused into the myocardium of porcine models just past the second diagonal of the LAD as shown in FIG. 1. The infusion rate was 1 mL/min. and the total number of particles was varied, as was the average particle size. The coronary blood flow recovery post-infusion was measured for each bolus administered.

FIGS. 15-18 illustrate the coronary blood flow recovery post-infusion for a variety of different particle sizes and total particle number.

Figure 15:
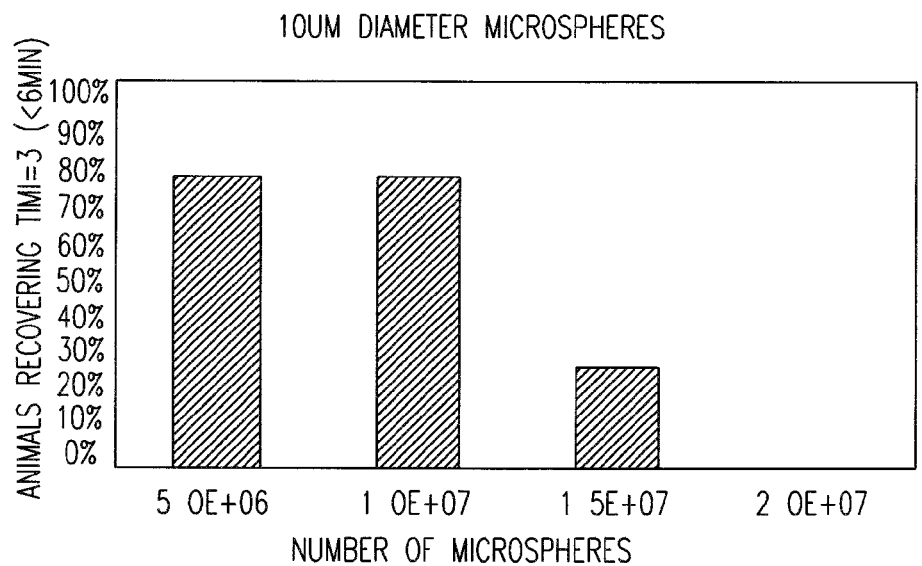
FIG. 15-18 illustrate coronary blood flow recovery post-infusion of incremental discrete doses of particles.

FIG. 15 is a graph illustrating the affect on coronary blood flow recovery post-infusion of microparticles having an average particle size of about 10 microns. As can be seen from the graph, up to about $1 \times 10^7$ microparticles may be delivered in a single bolus without having a significant impact on coronary blood flow.

Figure 16:
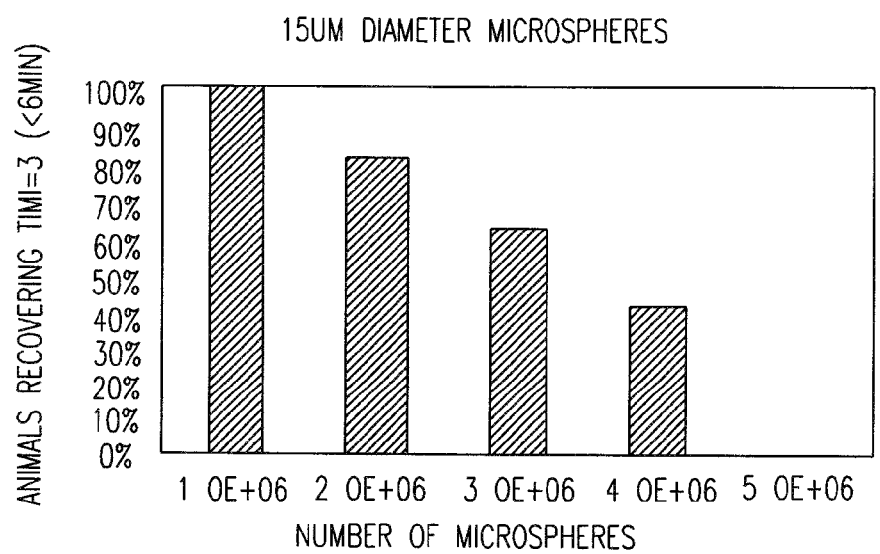

FIG. 16 is a graph illustrating the affect on coronary blood flow recovery post-infusion of microparticles having an average particle size of about 15 microns. As can be seen from the graph, up to about $2 \times 10^6$ microparticles may be delivered in a single bolus without having a significant impact on coronary blood flow.

Figure 17:
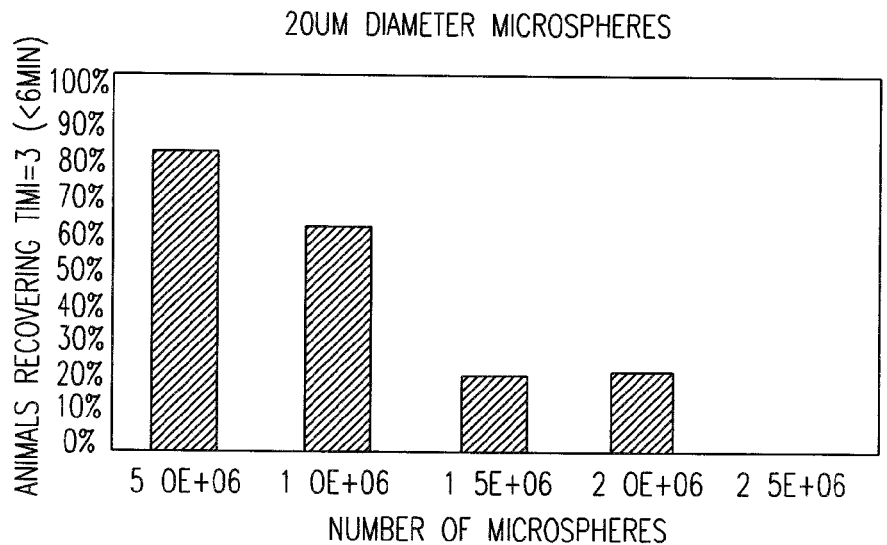

FIG. 17 is a graph illustrating the affect on coronary blood flow recovery post-infusion of microparticles having an average particle size of about 20 microns. As can be seen from the graph, up to about $1 \times 10^6$ microparticles may be delivered in a single bolus without having a significant impact on coronary blood flow.

Figure 18:
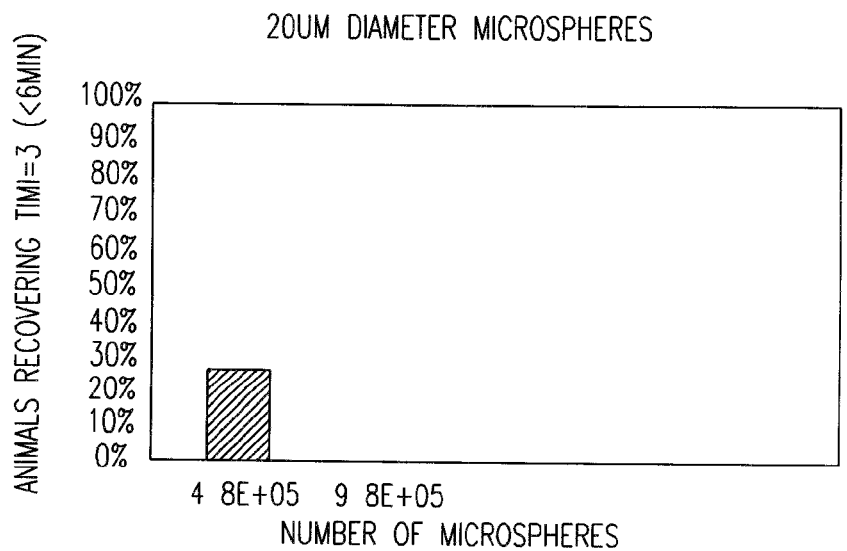

A mixed particle size distribution of between about 10 and about 25 microns is illustrated in FIG. 18. The coronary blood flow recovery post-infusion was negatively impacted with a total particle number of less than $5 \times 10^5$. This may indicate that particle sizes of larger than about 20 microns has a negative impact on coronary blood flow post-infusion.

Figure 19:
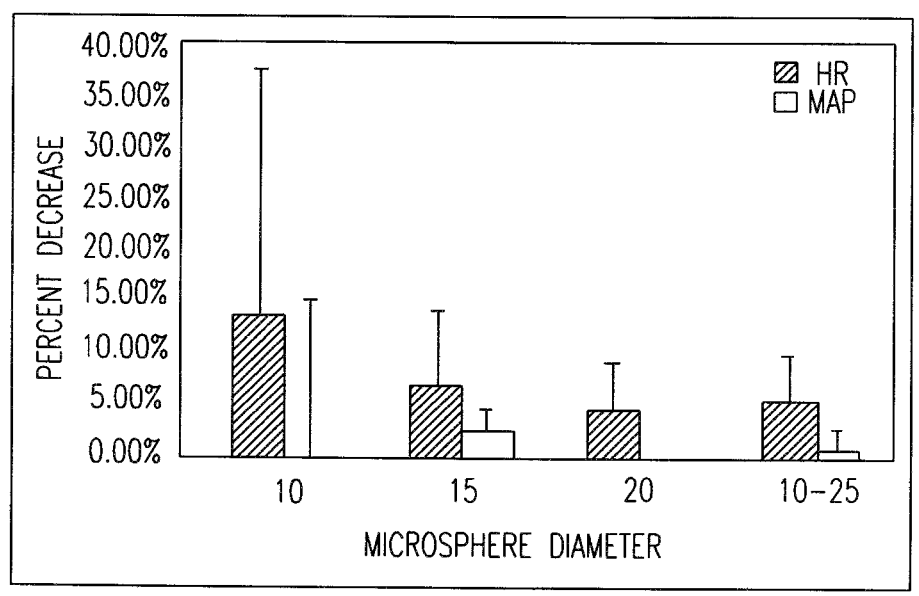
FIG. 19 illustrates a change in heart rate (HR) and mean arterial pressure (MAP) after infusion of microspheres of various diameters.

FIG. 19 is a graph illustrating blood pressure and mean arterial pressure pre- and post-infusion. Particle sizes between about 10 and about 25 microns had an insignificant impact on the blood pressure and mean arterial pressure post-infusion.

Figure 20:
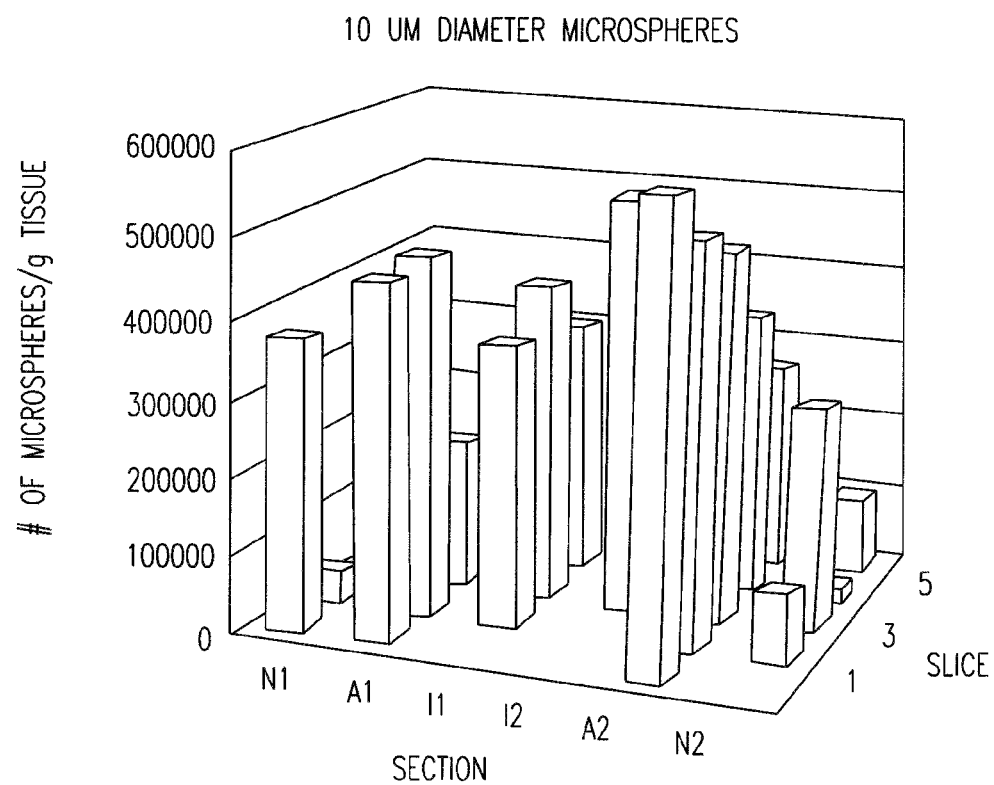
FIG. 20-22 illustrate the distribution of microparticles of various diameter sizes in an infarcted myocardium after infusion.
Figure 21:
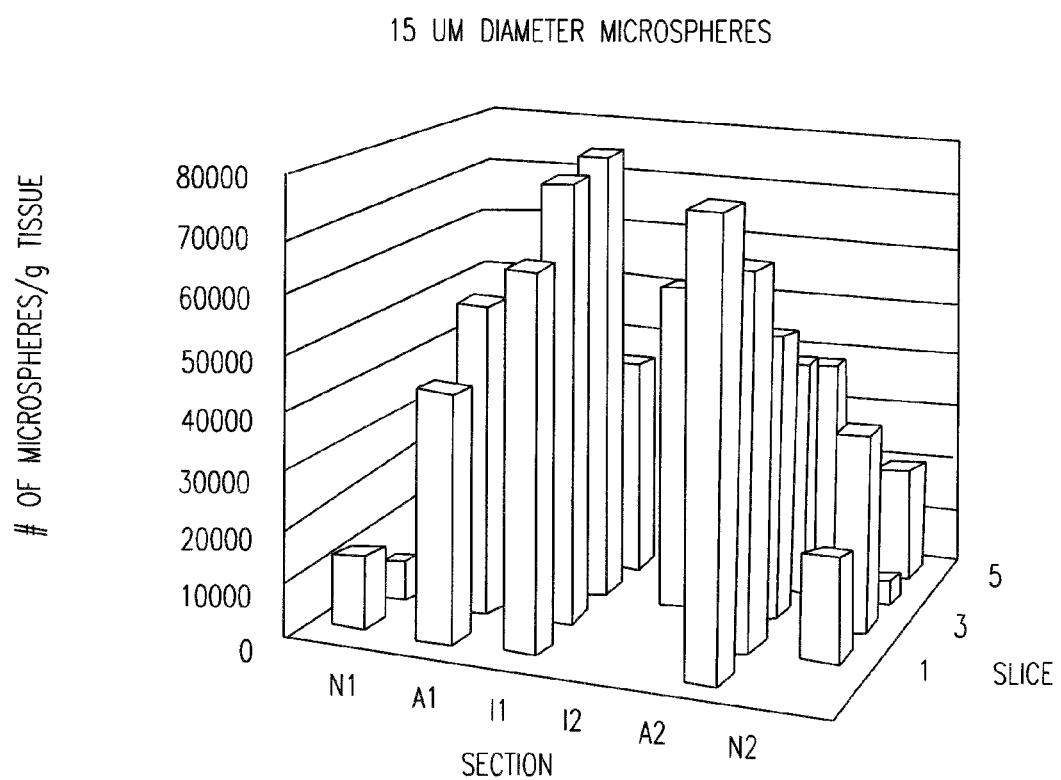
Figure 22:
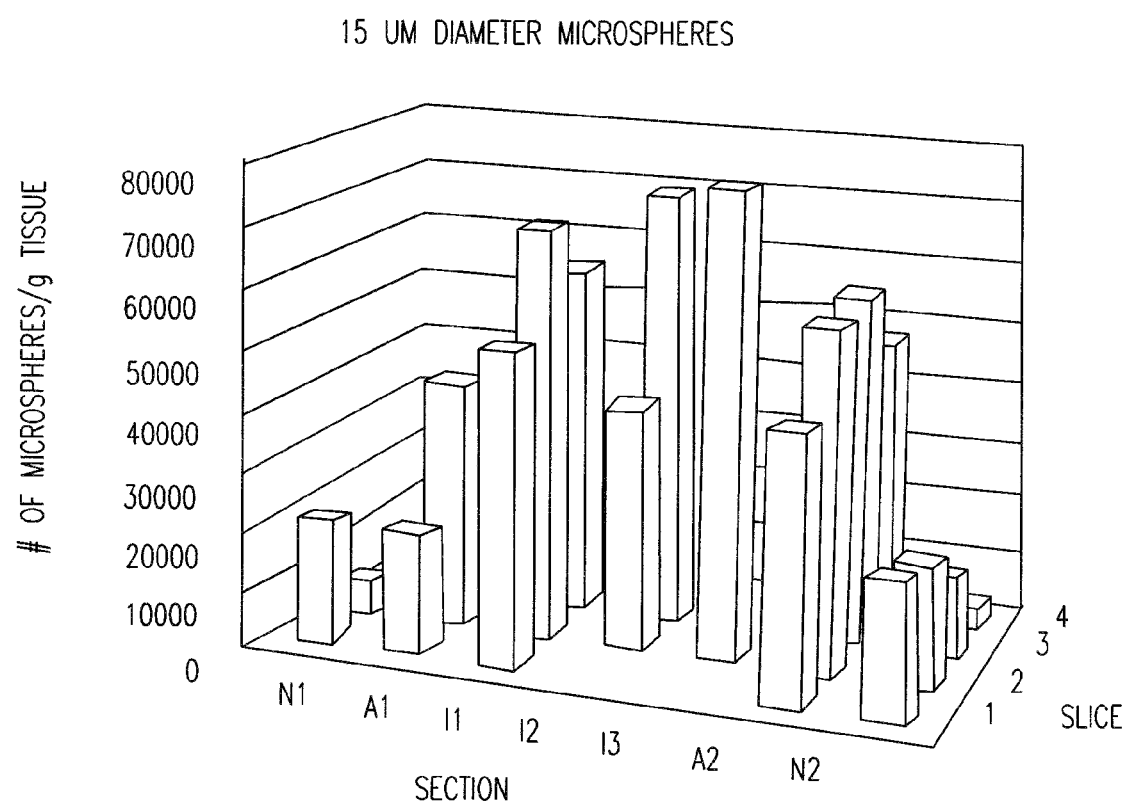

FIGS. 20-22 are 3D bar graphs illustrating the distribution of the microparticles in infarcted myocardium. In each graph
N1 and N2 indicate normal myocardium;
A1 and A2 indicate adjacent infarct with normal and infarcted areas;
I1 and I2 indicate infarcted myocardium;
N1 is toward the septum;
Slice 1 is just above the apex of the heart with subsequent slices going up to the site of infusion at the second diagonal of the LAD.

FIG. 20 illustrates that microparticles having an average particle size of about 10 microns are well-distributed in the infarcted myocardium.

FIG. 21 illustrates that microparticles having an average particle size of about 15 microns are well-distributed in the infarcted myocardium.

FIG. 22 illustrates that microparticles having an average particle size of about 20 microns are well-distributed in the infarcted myocardium Furthermore, little or no microparticles were found in the lung or liver of the porcine models in total numbers of less than about 10 microparticles per gram of tissue.

No detectable quantities of microparticles between about 10 microns and 20 microns in size were found in the circulating blood post-infusion.

Figure 23:
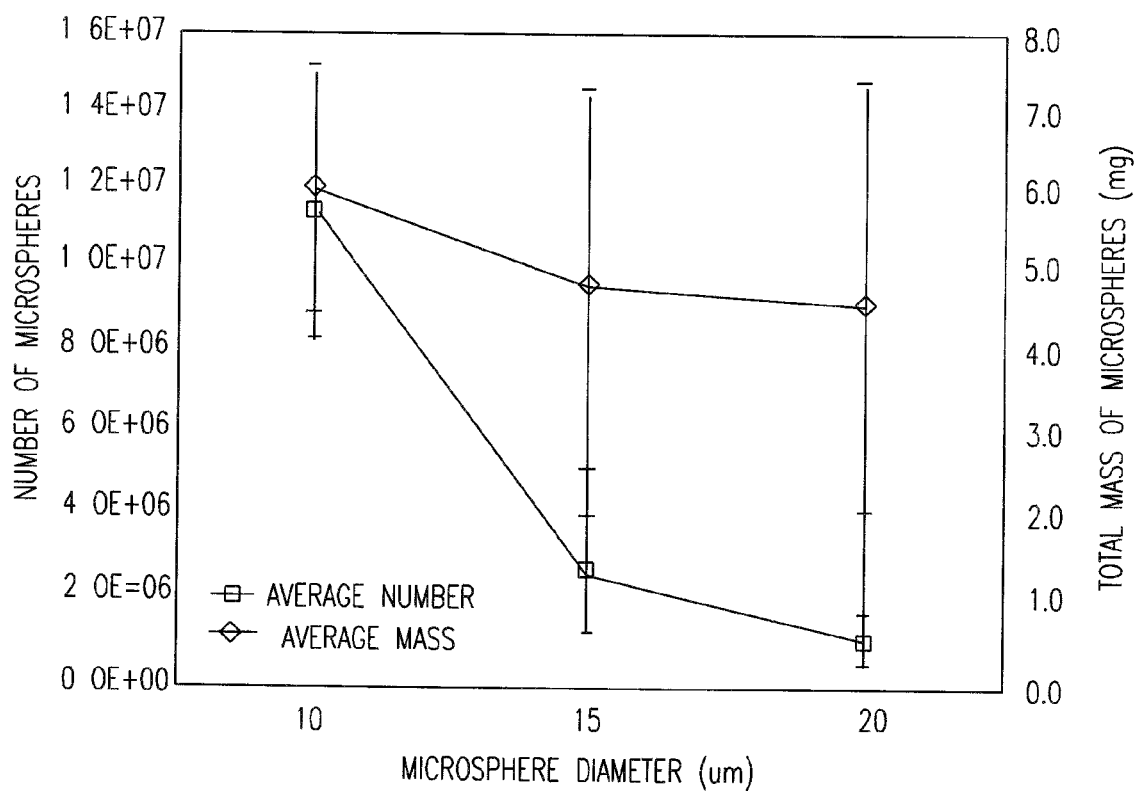
FIG. 23 is a graph summarizing dose feasibility for various particle sizes based on the average number of drug-loaded particles infused and the total mass of particles at the maximum tolerated dose as defined by recovery of normal coronary blood flow in a porcine model within 6 minutes.

FIG. 23 is a graph summarizing dose feasibility for various average particle sizes based on the average number of microparticles infused and the total mass of microparticles at the maximum tolerated dose. The maximum tolerated does in the total number of microparticles that could be infused where the porcine model was able to recovery normal coronary blood flow (TIMI=3) within 6 minutes post-infusion.

For this particular example, the optimum total mass of microparticles delivered by coronary infusion in a single bolus was found to be about 10 mg.

The above disclosure is intended to be illustrative and not exhaustive. This description will suggest many variations and alternatives to one of ordinary skill in this art. Those familiar with the art may recognize other equivalents to the specific embodiments described herein which equivalents are also intended to be encompassed by the claims.

The invention claimed is:

1. A method for modulating remodeling of an infarct region of a myocardium, the method comprising:
   identifying an infarct region within a ventricle of the myocardium;
   infusing microparticles into a coronary artery to said infarct region with a catheter assembly, the catheter assembly comprising at least one elongate catheter shaft having an inner surface defining a lumen, said microparticles are covalently bonded to the inner surface through a linkage which is cleavable by enzymes or in the presence of water, said microparticles comprising at least one therapeutic agent effective for modulating remodeling of the infarct region, said microparticles having a mixed diameter range of about 1 micron to about 45 microns, and
   perfusing a liquid comprising enzymes or water through said lumen of said at least one catheter shaft.

2. The method of claim 1 wherein the mean diameter of said microparticles is between about 10 microns and about 25 microns.

3. The method of claim 1 wherein said microparticles have an average particle size of about 10 microns to about 20 microns.

4. The method of claim 1 wherein said at least one therapeutic agent is encapsulated by a solid polymer composition.

5. The method of claim 4 wherein said solid polymer composition comprises at least one member selected from the group consisting of polyhydroxyalkanoates, polylactones, poly(L-lactic acid) (PLA), poly(glycolic acid), poly(D,L-lactic acid), poly(lactide-co-glycolide), polydioxanone, polyorthoesters, polyanhydrides, poly(glycolic acid-co-trimethylene carbonate), polyphosphoesters, polyphosphoester urethanes, poly(amino acids), cyanoacrylates, poly(trimethylene carbonate), poly(iminocarbonate), copoly(ether-esters), polyalkylene oxalates, polyphosphazenes, polyalkylene glycols, polyvinyl alcohols, biomolecules and mixtures thereof.

6. The method of claim 4 wherein said solid polymer composition comprises at least one bioerodable polymer.

7. The method of claim 4 wherein said solid polymer composition is bioerodable.

8. The method of claim 1 wherein said infarct region is within the left ventricle and said coronary artery is the left anterior descending coronary artery or the circumflex branch of the coronary artery.

9. The method of claim 1 wherein said infarct region is in the right ventricle, the left ventricle, the right atrium, or the sinoatrial node and the coronary is the right coronary artery.

10. The method of claim 1 wherein said at least one therapeutic agent is a member selected from the group consisting of therapeutic agents effective for inhibiting matrix metalloproteinase, therapeutic agents effective for mediating renin angiotensin aldosterone system pathways, therapeutic agents effective for inhibiting myocyte death and therapeutic agents effective for promoting myocyte survival, cardiac fibrosis and myocyte hypertrophy.

11. The method of claim 1 wherein said method is performed concurrently with percutaneous coronary intervention.

12. The method of claim 1 comprising infusing a single bolus of said microparticles into said coronary artery, the total mass of said microparticles is about 10 mg or less.

13. The method of claim 1 comprising infusing a single bolus of said microparticles into said coronary artery, the total number of microparticles is between about $1 \times 10^6$ to about $1 \times 10^7$.

* * * * *